(12) United States Patent
Rao et al.

(10) Patent No.: US 6,583,175 B2
(45) Date of Patent: Jun. 24, 2003

(54) ALKYLXANTHATES AND USE OF ALKYLXANTHATES IN THE INTEGRATED PEST MANAGEMENT

(75) Inventors: Janapala Venkateswara Rao, Andhra Pradesh (IN); Yenamandra Venkateswarlu, Andhra Pradesh (IN); Kondapuram Vijaya Raghavan, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/820,731

(22) Filed: Mar. 30, 2001

(65) Prior Publication Data

US 2003/0022931 A1 Jan. 30, 2003

(51) Int. Cl.$^7$ ............... A61K 31/34; A61K 31/265; C07D 307/02; C07C 329/00
(52) U.S. Cl. ............ 514/461; 514/512; 549/473; 558/245; 558/246
(58) Field of Search ............... 558/246, 245; 549/473; 514/461, 512

(56) References Cited

U.S. PATENT DOCUMENTS 3,845,092 A * 10/1974 Schneider et al. .......... 558/245
3,919,281 A * 11/1975 Marubashi et al. ......... 558/245
5,011,965 A *  4/1991 Saphores et al. .......... 558/245

OTHER PUBLICATIONS

"Pesticide use in India doubled in eight years", *Pesticides World*, Apr.–May, 1998, p. 43.
"Pesticides—Banned elsewhere, used in India", Indian Express Newspapers (Bombay) Ltd., Saturday Dec. 9, 2000.
Venkateswarlu et al., "Ethylene Bis (Alkylxanthate) form a Green Alga *Dictyosphaeria Favulosa* #", Tetrahedron Letters, vol. 34, No. 22, pp. 3633–3634, 1993.

* cited by examiner

Primary Examiner—Alan L. Rotman
Assistant Examiner—Raymond Covington
(74) Attorney, Agent, or Firm—Oliff & Berridge, PLC (57) ABSTRACT

This invention relates to novel alkylxanthates of formulae 1 to 3 and use of alkylxanthates of formulae 1 to 6 in the integrated pest management, more specifically alkyl xanthates are used as insect growth regulators for pest management in agricultural fields no or less environmental impact.

28 Claims, 10 Drawing Sheets

(2 of 10 Drawing Sheet(s) Filed in Color)

FIG. 1

Methylene bis (tetrahydrofurfurylaxanthate)

| | |
|---|---|
| Physical state | : Colorless liquid |
| Molecular formula | : $C_{13}H_{20}O_4S_4$ |
| $^1$H NMR | : (CDCl$_3$, 200 MHz) δ 1.70 (2H, m), 1.95 (2H, m), 3.71 (2H, m), 4.20 (1H, m), 4.55 (2H, t) and 4.78 (1H, s). |
| IR (Neat) | : $\nu_{max}$ (KBr) 2920, 1470, 1235 and 1140 cm$^{-1}$ |
| EIMS (70 eV) | : m/z 368 |
| UV (MeOH) | : $\lambda_{max}$ (MeOH) 217 (ε 11150), 242 (1650), 270 nm (19160) |

FIG. 2 m-Fluorobenzyl n-butylxanthate

| | |
|---|---|
| Physical state | : Pale yellow liquid |
| Molecular formula | : $C_{12}H_{15}FOS_2$ |
| $^1$H NMR | : (CDCl$_3$, 200 MHz) δ 1.0 (3H, m), 1.42 (2H, m) 1.75 (2H, m), 4.60 (2H, t, $J$ = 7.0 Hz), 4.35 (2H, s) and 6.95-7.20 (4H, m). |
| IR (Neat) | : $\nu_{max}$ 2960, 2931, 1615, 1590, 1460, 1240 and 1045 cm$^{-1}$ |
| EIMS (70 eV) | : *m/z* 258 |
| UV (MeOH) | : $\lambda_{max}$ 210 (ε 37105), 218 (35660), 280 nm (27354) |

FIG. 3 m-Fluorobenzyl isobutylxanthate

| | |
|---|---|
| Physical state | : Pale yellow liquid |
| Molecular formula | : $C_{12}H_{15}FOS_2$ |
| $^1$H NMR | : (CDCl$_3$, 200 MHz) δ 1.0 (6H, d, $J$ = 7.0 Hz), 2.12 (1H, m), 4.34 (4H, brs) and 6.92-7.22 (4H, m). |
| IR (Neat) | : $\nu_{max}$ 2964, 2937, 1620, 1585, 1472, 1230, 1165 and 1030 cm$^{-1}$ |
| EIMS (70 eV) | : $m/z$ 258 |
| UV (MeOH) | : $\lambda_{max}$ 214 (ε 37190), 220 (35674) and 274 nm (27378) |

FIG. 4

Ethylene bis (isobutylxanthate)

| | |
|---|---|
| Physical state | : Colorless solid |
| Molecular formuila | : $C_{12}H_{22}O_2S_4$ |
| $^1$H NMR | : (CDCl$_3$, 200 MHZ) δ 1.0 (6H, d, $J$ = 7.5 Hz), 2.15 (1H, m), 3.42 (2H, m) and 4.35 (2H, d, $J$ = 7.5 Hz). |
| IR (Neat) | : $v_{max}$, (KBr) 2950, 1465, 1235, 1200, and 1140 cm$^{-1}$ |
| EIMS (70 eV) | : $m/z$ 326 |
| uV (MeOH) | : $\lambda_{max}$ (MeOH) 217 (ε 12725), 232 (14766) and 278nm (20048) |

FIG. 5

Methylene bis (n-butylxanthate)

| | |
|---|---|
| Physical state | : Colorless solid |
| Molecular formula | : $C_{11}H_{20}O_2S_4$ |
| $^1$H NMR | : (CDCl$_3$, 200 MHz) δ 0.98 (3H, t, $J$ = 7.5 Hz), 1.45 (2H, m), 1.78 (2H, m), 4.58 (2H, t, $J$ = 7.5 Hz) and 4.80 (1H, s). |
| IR (Neat) | : $\nu_{max}$ (KBr) 2955, 1470, 1230, 1195 and 1130 cm$^{-1}$ |
| EIMS (70 eV) | : $m/z$ 312 |
| UV (MeOH) | : $\lambda_{max}$ (MeOH) 215 (ε 12000), 235 (15500), 275 nm (19260) |

FIG. 6 p-Xylene bis (n-butylxanthate)

| | |
|---|---|
| Physical state | : Colorless solid |
| Molecular formula | : $C_{18}H_{26}O_2S_4$ |
| $^1$H NMR | : ($CDCl_3$, 200 MHz) δ 0.98 (3H, t, $J$ = 7.0 Hz), 1.45 (2H, m), 1.80 (2H, m), 4.32 (2H, s), 4.60 (2H, t, $J$ = 7.0 Hz) and 7.30 (2H, s). |
| IR (Neat) | : $\nu_{max}$ (KBr) 3160, 2970, 1620, 1215 and 1060 $cm^{-1}$ |
| EIMS (70 eV) | : $m/z$ 402 |
| UV (MeOH) | : $\lambda_{max}$ (MeOH) 210 (ε 30150), 222 (26135), 270 nm (20140) |

Methylene bis (tetrahydrofurfurylxanthate)
20μg/insect p-Xylene bis (n-butylxanthate)
(30μg/insect)

Standard Azadiractin m-Fluorobenzyl isobutylxanthate

FIG. 7

Glimpses of the results

Control pupae and normal adult formation in polyphagous pest *Spodoptera litura*

Control Larvae     Xanthate treated larvae     Larval Mortality
(Topical application)

Methylene bis (n-butylxanthate) 25µg/insect     Methylene bis (tetrahydrofurfurylxanthate) 30µg/insect     m-Fluorobenzyl n-butylxanthate 35µg/insect

ALKYLXANTHATES AND USE OF ALKYLXANTHATES IN THE INTEGRATED PEST MANAGEMENT

FILED OF THE INVENTION

The present invention relates to novel alkylxanthates of formulae 1 to 3 and use of alkylxanthates of formulae 1 to 6 in the integrated pest management, more specifically alkyl xanthates are used as insect growth regulators for pest management in agricultural fields no or less environmental impact.

BACKGROUND AND PRIOR ART REFERENCES

Many small scale farmers are illiterate and believe in the usage of high volumes, high pressure, and high doses of pesticide as the most suitable way of crop protection, these practices have resulted in many environmental problems such as effect on non-target species, pesticide residue accumulation, variable selectivity, development of resistant in pests, ecological imbalance by elimination of natural predators as well as and environment pollution. More than 50% of the pesticides used in third world countries are globally banned and 95% of the used by the public health sector also find restricted use in other nations (News corner, Pesticide World, 1998). There are 33 pesticides, which have been banned in advanced countries, but they are allowed to be imported and used in third world countries (Insecticides Act, 1968 and Indian Express Newspaper January, 2000). In order to restrict the use of banned pesticides, they must be replaced with suitable pesticides that must be target specific, non-toxic to other species, easily biodegradable and less persistent. Hence, the advanced countries are mainly concentrated to identify the IV generation of insecticides, which are highly effective and generally selective agents derived for tactical skills. It requires more management expertise which are far friendlier to the total environment including the biological control organisms.

The applicants have isolated a Ethylene Bis (isobutylxanthate) (1) from a green alga *Dictyosphaeria favulosa* (Venkateswarlu et al, 1993). It was tested against various aquatic stages of *Aedes aegypti* mosquito, which is a yellow fever vector. The compound 1 exhibited larvicidal and insect growth regulatory activity in dose dependent mannar (Venkateswarlu Rao et al., 1995). Around thirty-five analogues were synthesised and tested against agricultural polyphagous lepidopteron pests. Among them four analogues have been identified as good antifeedant and insect growth regulators. Two of the compounds from the four analogues are totally new structures and remaining two are structurally known but the activity was identified for the first time.

1

Compound I: Ethylene Bis (isobutylxanthate)
Physical state: Colorless solid
M.P.: 40–42° C.
Molecular formula: $C_{12}H_{22}O_2S_4$ EIMS (70 eV): m/z 326

Elemental analysis: Found: C 44.15%, H 6.90%, S 39.15% Required: C 44.13%, H 6.79%, S 39.28%

IR(KBr): $V_{max}$(KBr) 2950, 1465, 1235, 1200, and 1140 $cm^{-1}$

UV(MeOH): $\lambda_{max}$(MeOH) 217 ($\epsilon$ 12735), 232 (14766) and 278 nm (20048)

$^1$H NMR: (CDCl$_3$, 200 MHz) δ 1.0 (6H, d, J=7.5 Hz), 2.15 (1H, m),

In 1950 S. V. Zhuravlev, reported the synthesis of ethylene dixanthates (2–5). Heating the mixture of 4.7 gms (CH$_2$Br$_2$)$_2$ and EtOCS$_2$K in ethanol on a steam bath gave ethylene dixanthate (yield 90%). In which compounds 2 and 5 possess a moderate insecticidal activity against lice.

In 1954 Yamasaki, reported the synthesis of organophophorus compounds (xanthgenates). A series of xanthogenates (6–10) were synthesized in three ways.

A)

B)

C)

here M=alkali metal

6 R'=Me; R=Me
7 R'=n-propyl; R=ethyl
8 R'=ethyl; R=ethyl
9 R'=sopronyl; R=ethyl
10 R'=n-butyl; R=ethyl

In 1950 S. V. Zhuravlev, reported the synthesis of p-xylene dixanthates. MeOCS$_2$K reacted with p-C$_6$H$_4$(CH$_2$Cl)$_2$ in ethanol gave p-xylene bis (methylxanthate) (yield 75.5%). A series of p-xylene bis xanthates has been synthesized (11–20). All these bis xanthates are insecticides with low order of activity.

11 R=ethyl
12 R=n-butyl
13 R=isobutyl
14 R=octyl
15 R=isooctyl
16 R=nonyl
17 R=decyl
18 R=cyclohexyl
19 R=phenethyl
20 R=benzyl The dixanthates were dissolved in refined kerosene to form a 25% solution was used as a efficient defoliants for cotton plants (Cupery, 1958).

Etylene Bis (isopropylxanthate) (21) and ethylene bis (isobutylxanthate) (1) were used as noncorrosive antiseize lubricating oil additives (Khalikov and Vinogradova, 1964).

1   R = isobutyl
21  R = isopropyl

Methylene bisxanthates are used as collector reagents in the froth flotation of sulfide minerals (Saphores, et al., 1991).

Ten newly synthesized organo phosphorus derivatives containing alkyl xanthates were tested for their antifungal activity against *Colletotrichum falcatum, Fusarium oxisporium, Curvularia pallescens* (sugarcane pathogens). The O,O-diethyl thio phosphate derivatives exhibited 100% mycelial inhibition against all the test fungi at 1000 ppm. All thio phosphate derivatives showed fungistatic effects at a minimum inhibitory concentration of 1000 ppm. These derivatives also proved better than currently used synthetic fungicides (Senguptha et al., 1998).

In the course, the applicants have synthesized ethylene bis (isobutylxanthate) and its analogues. In which compound 25, 27 and 28 are newly synthesized compounds and these compounds were tested for antifeedant and larvicidal activities.

OBJECTS OF THE INVENTION

The main object of the invention is to provide novel alkylxanthates for agricultural applications.

In another object of the invention is to provide a new use of novel alkylxanthates for use in integrated pest management.

In still another object is to provide a new activity of alkylxanthates for use in integrated pest management.

In yet another object is to provide a process for the preparation analogues of alkyl xanthates useful as an antifeedent and as insect growth regulators.

In yet another object is to provide a composition useful as an insect growth regulator and antifeedant for the integrated pest management.

SUMMARY OF THE INVENTION

The present invention relates to novel alkylxanthates of formulae 1 to 3 and use of alkylxanthates of formulae 1 to 6 in the integrated pest management, more specifically alkyl xanthates are used as insect growth regulators for pest management in agricultural fields no or less environmental impact.

BRIEF DESCRIPTION OF THE ACCOMPANYING DRAWINGS

The patent or application file contains at least one drawing executed in color. Copies of this patent application publication with color drawings will be provided by the Office upon request and payment of the necessary fee.

DETAILED DESCRIPTION OF THE INVENTION

Figure 1:
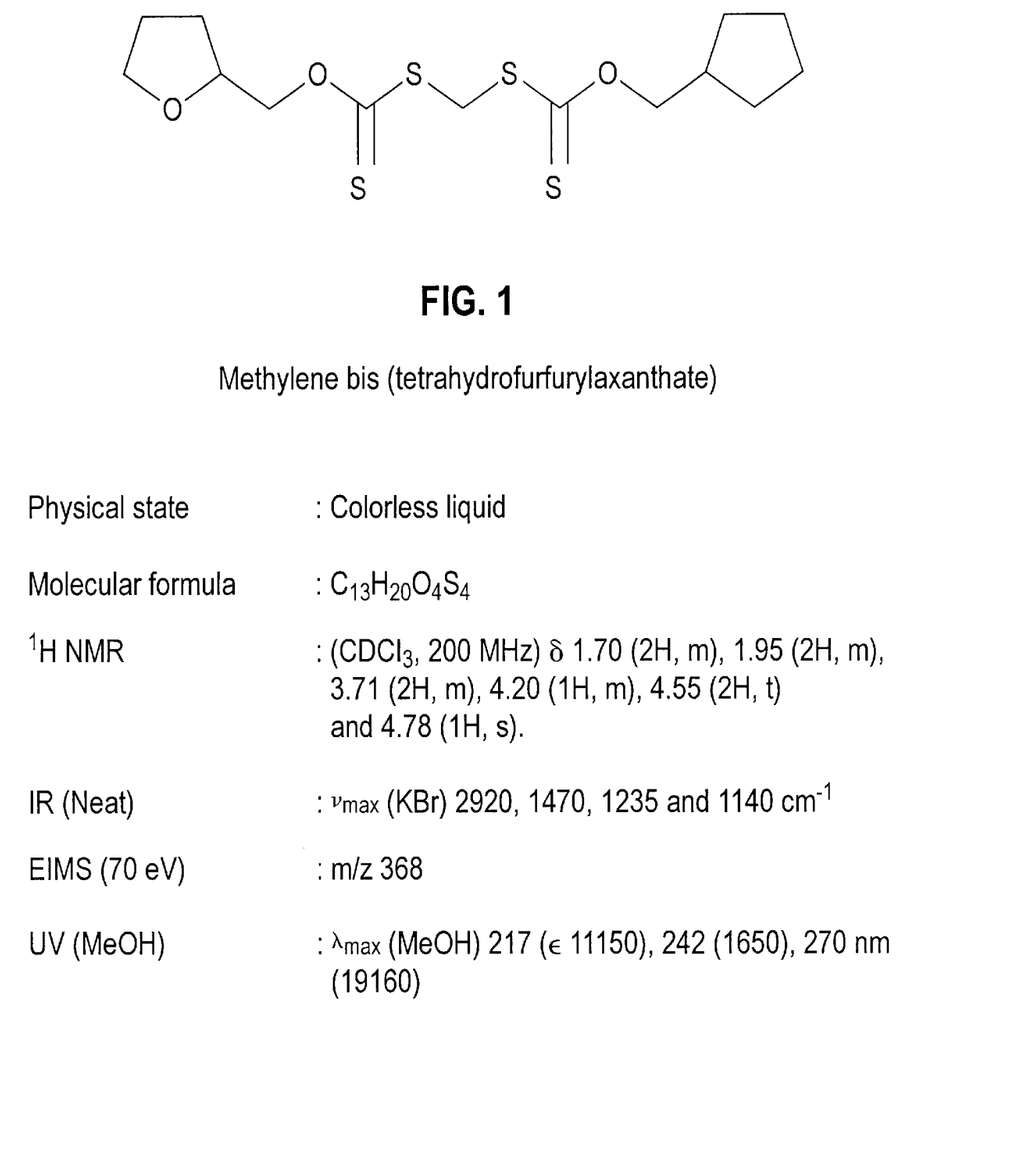
FIG. 1 shows structure of Methylene bis (tetrahydrofurfurylxanthate.
Figure 2:
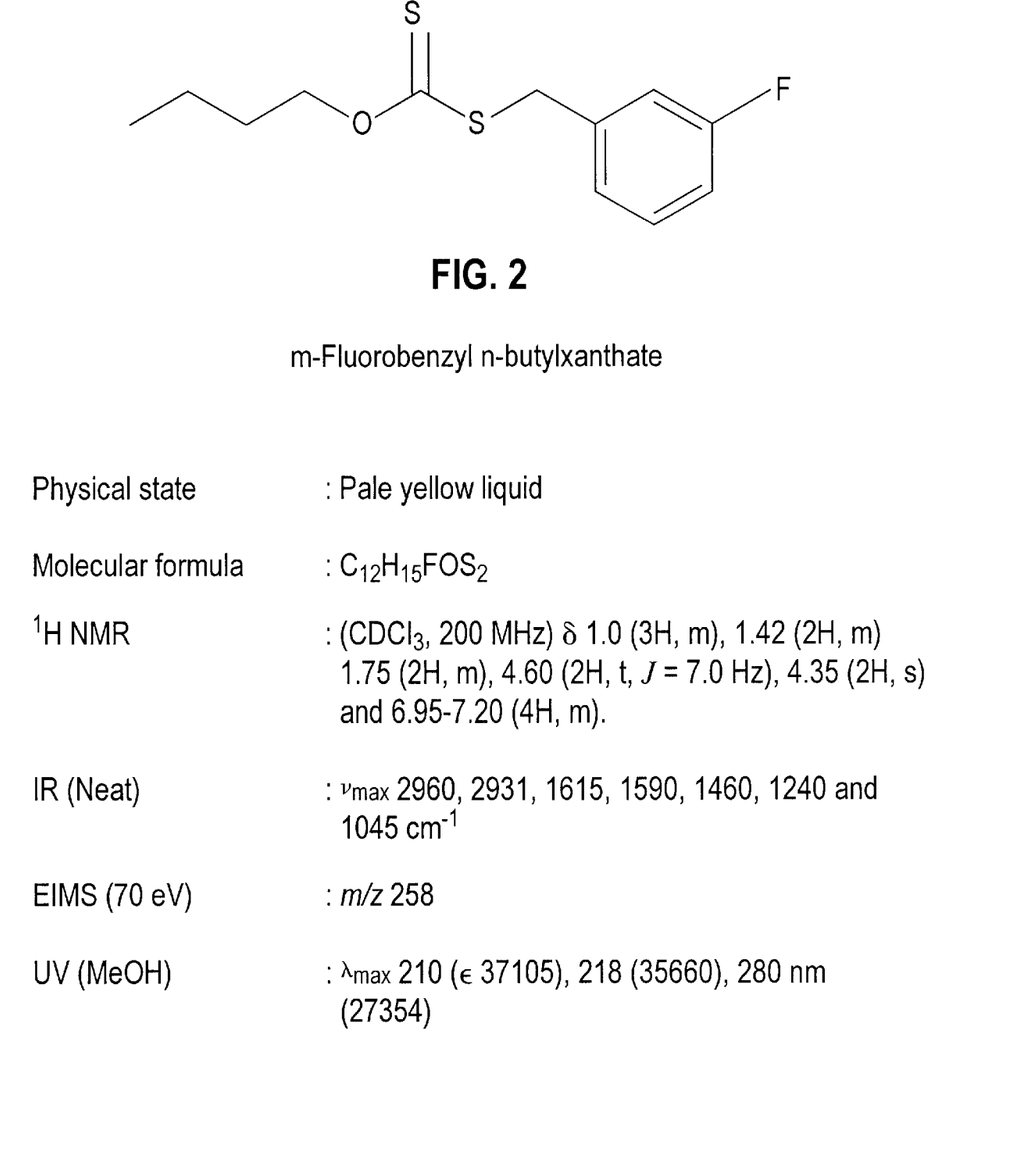
FIG. 2 shows structure of m-Fluorobenzyl n-butylxanthate
Figure 3:
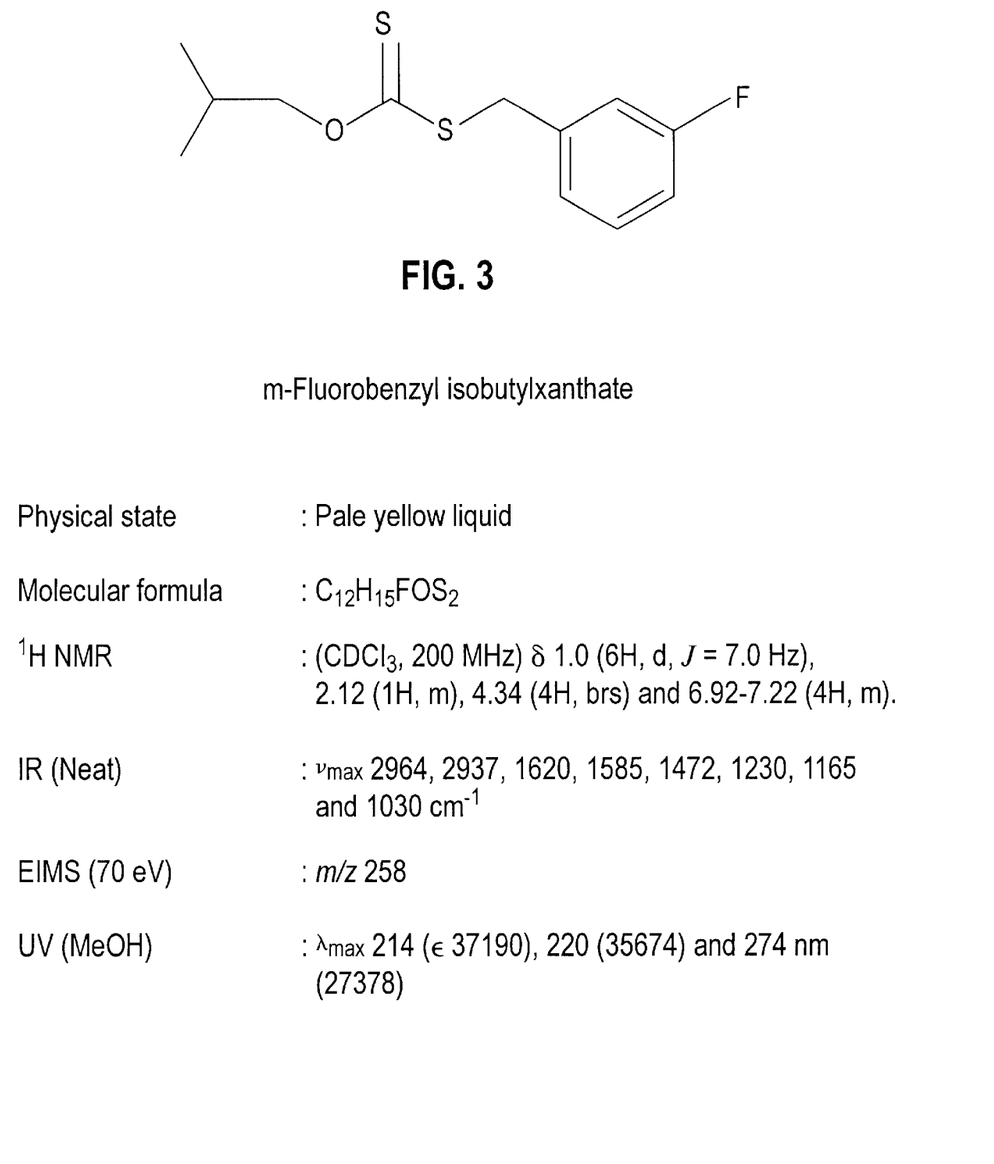
FIG. 3 shows structure m-Fluorobenzyl isobutylxanthate
Figure 4:
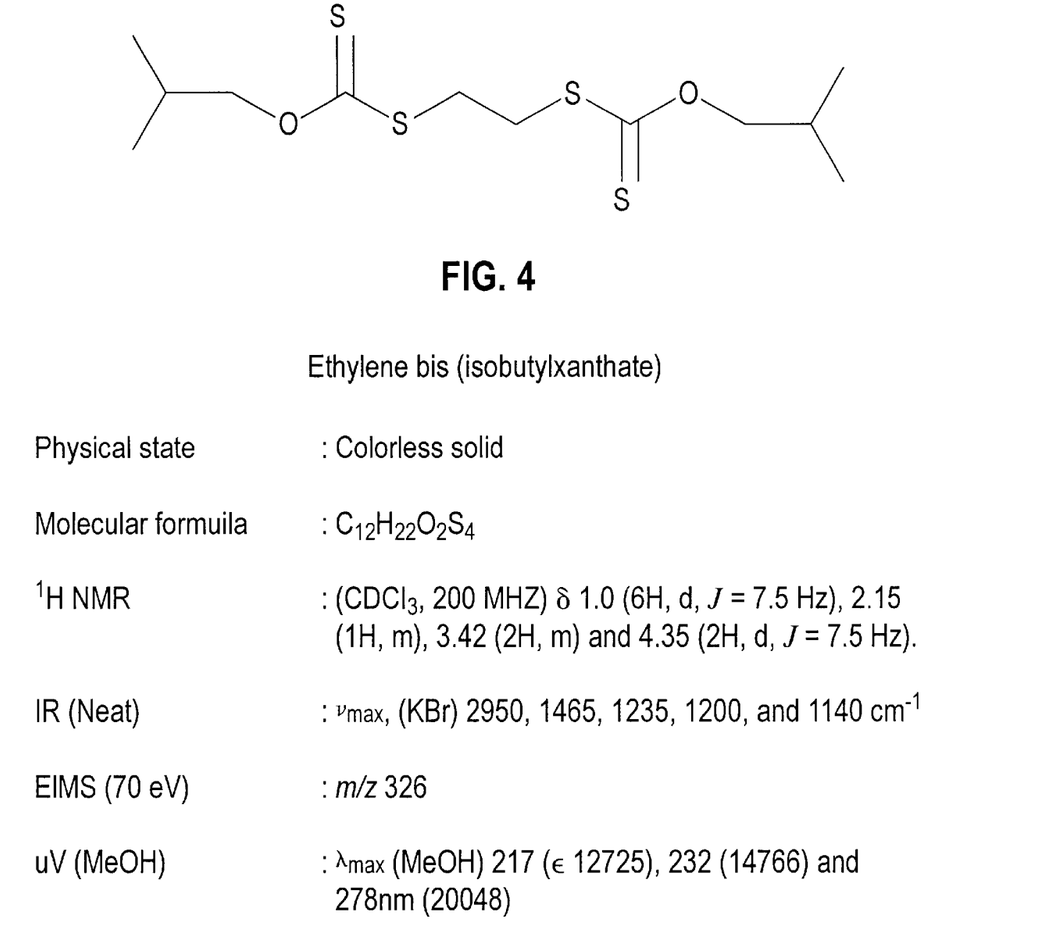
FIG. 4 shows structure Ethylene bis (isobutylxanthate
Figure 5:
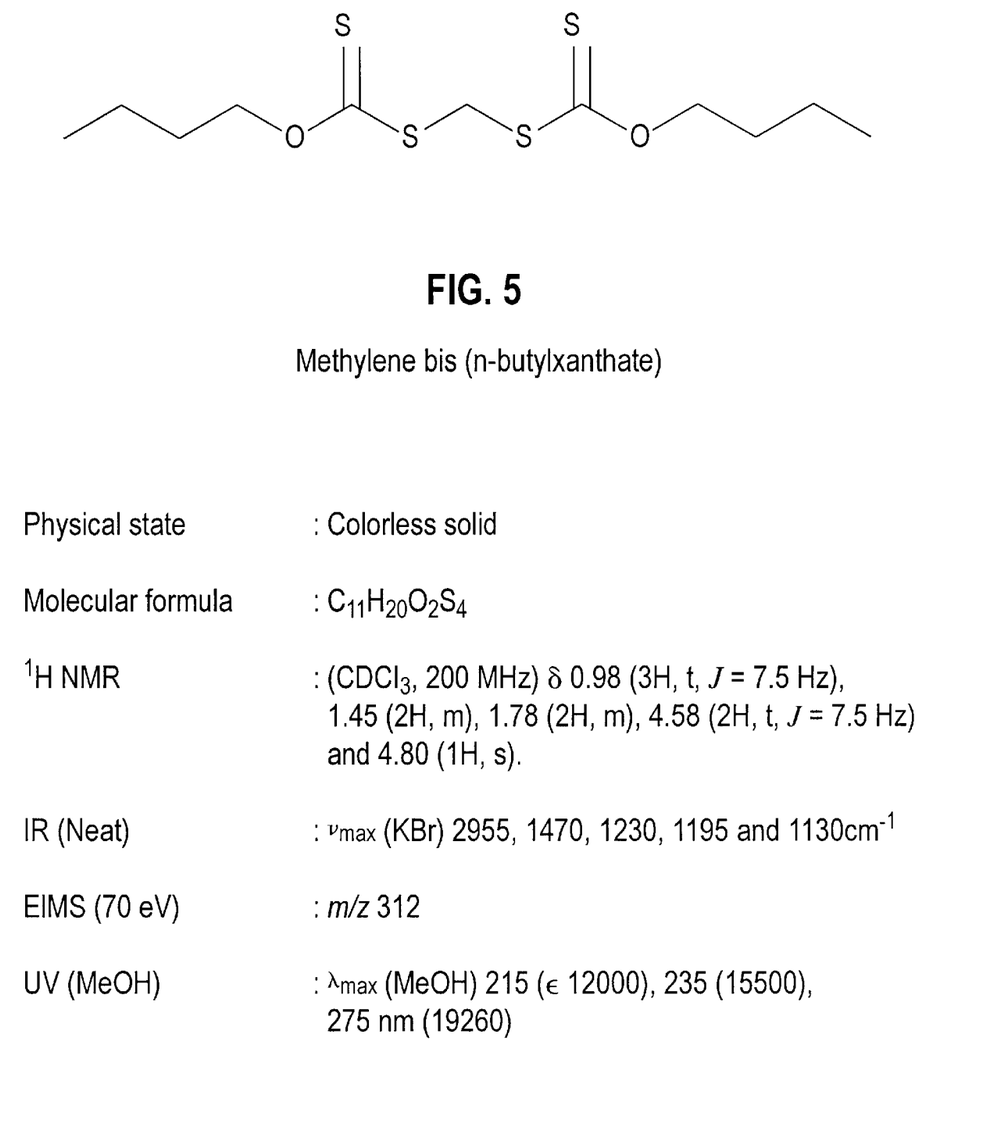
FIG. 5 shows structure of Methylene bis (n-butylxanthate)
Figure 6:
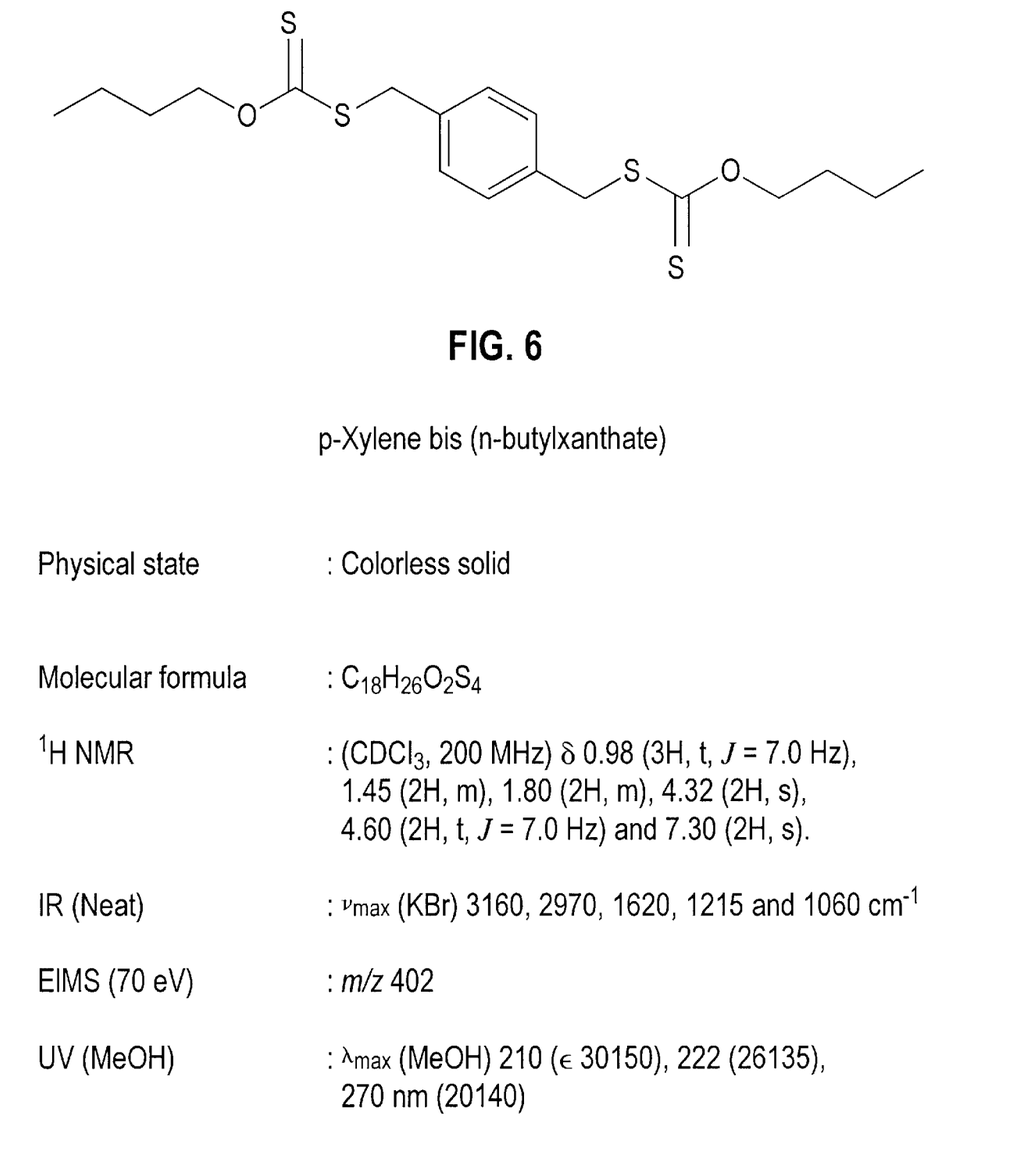
FIG. 6 shows structure p-Xylene bis (n-butylxanthate)
Figure 7:
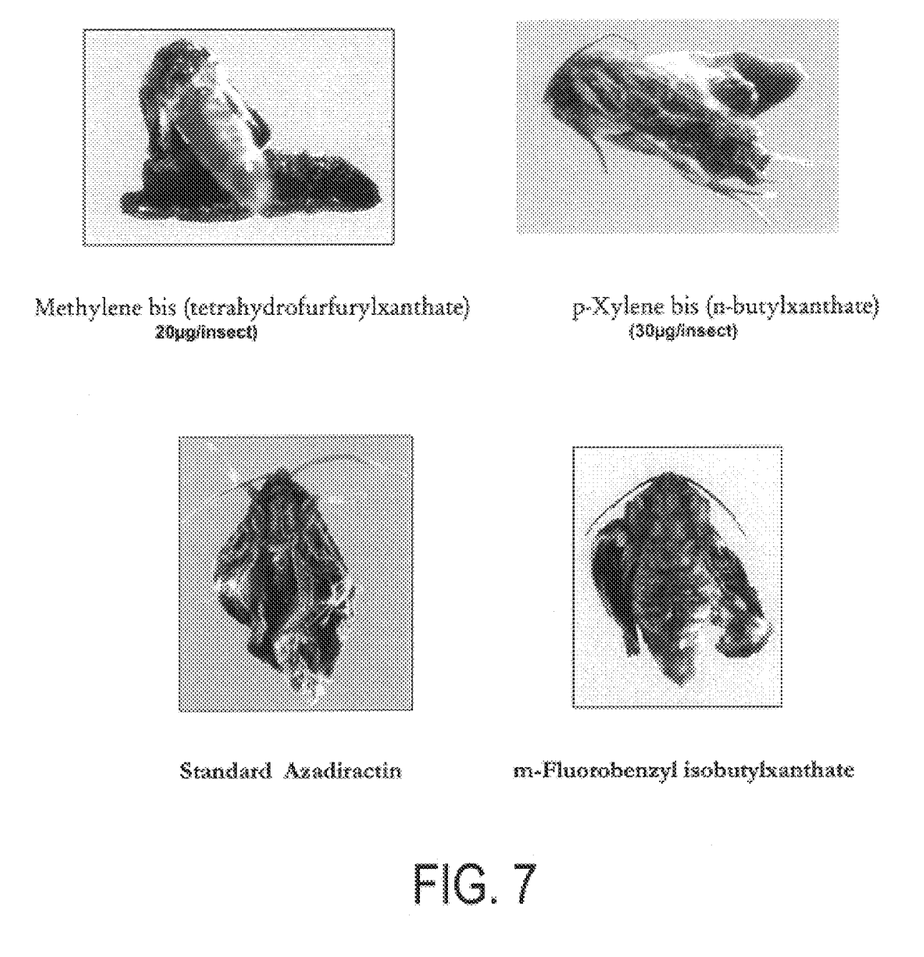
FIGS. 7 and 8 shows glimpses of the results.
Figure 8:
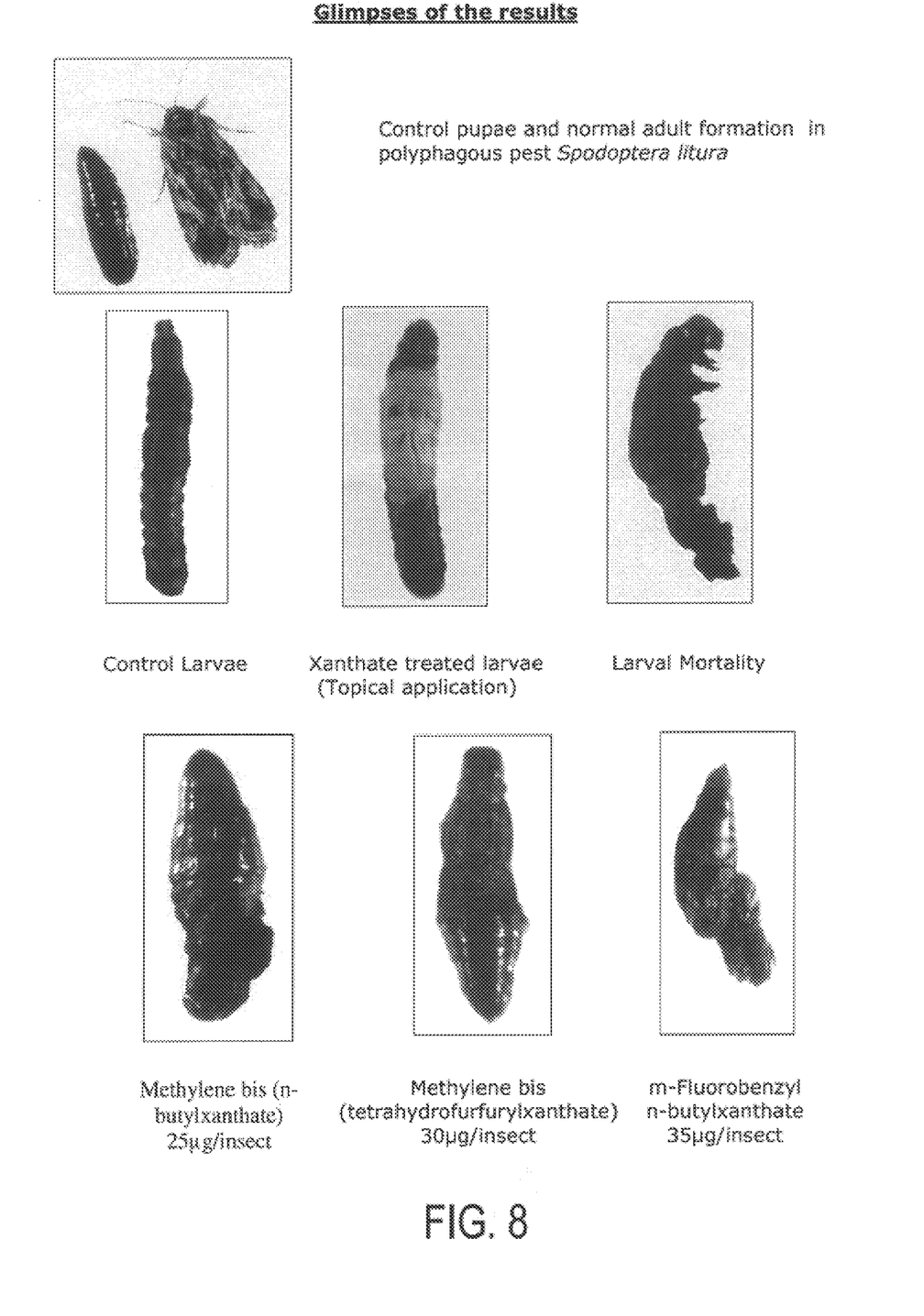

The present invention particularly relates to develop an Alkylxanthates as novel Insect Growth Regulators (IGR's) that are useful for integrated pest management. The alkylxanthates employed in the present invention was useful to maximize the lepidopteron pest infestation in agricultural fields with no or less environmental impact. These alkylxanthates as natural products are relatively uncommon in nature. We have been isolated a Ethylene Bis (isobutylxanthate) (1) from a green alga *Dictyosphaeria favulosa.* It was tested against various aquatic stages of *Aedes aegypti* mosquito, which is a yellow fever vector. The compound 1 exhibited larvicidal and insect growth regulatory activity in dose dependent mannar. The analogues of Alkylxanthates has been proved as insect growth regulators (IGR) against two different lepidopteron pests (*Spodoptera litura* and *Helicoverpa armigera*), as similar to Azadiractin (standard compound) a natural product isolated from neem seed kernel. They have simple structures unlike Azadiractin and possessing same kind of mode of action, which can be synthesized easily in the laboratory The present invention provides three novel compounds of alkylxanthates namely (i) methylene Bis (tetrahydrofurfuryl xanthate)

(ii) m-Fluorobenzyl n-butylxanthate and
(iii) m-Fluorobenzyl isobutylxanthate having the structural formulae as shown in FIGS. 1, 2 and 3 respectively of the accompanying drawings, for use in agricultural applications.

In an embodiment of the said compounds having the following properties on lepidopteron pest as
(a) larvicidal,
(b) antifeedant, and
(c) insect growth regulator.

In still another embodiment the novel compounds possess toxicity towards brine shrimps and mosquitoes.

In still another embodiment of the invention, the novel compounds controls the growth of the agricultural pests *Spodoptera litura*, and *Helicover armigera*.

In yet another embodiment the novel compounds used as insect growth regulator is ranging from 50 $\mu$g to 100 $\mu$g per insect, (topical application on III instar larvae) and 5 to 25 $\mu$g oral feeding.

In yet another embodiment the larval mortality rate is in the range between 50 to 90% when the above novel compounds are used.

In yet another embodiment of the invention, the amount of analogs of alkyl xanthates used for protecting the leafs are in the range between 15 to 50 micro grams per sq.cm of the leaf area.

In yet another embodiment, the novel compound methylene Bis (tetrahydrofurfuryl xanthate) is a colorless liquid and the molecular formula is $C_{13}H_{20}O_4S_4$ and having the following properties:
Physical state: Colorless liquid
Molecular formula: $C_{13}H_{20}O_4S_4$
$^1$H NMR: (CDCl$_3$, 200 MH$_z$) $\delta$1.70 (2H, m), 1.95 (2H, m), 3.71 (2H, m), 4.20 (1H, m), 4.55 (2H, t) and 4.78 (1H, s).
IR (Neat): $\nu_{max}$ (KBr) 2920, 1470, 1235 and 1140 cm$^{-1}$
EIMS (70 eV): m/z 368
UV (MeOH): $\lambda_{max}$ (MeOH) 217 ($\epsilon$ 11150), 242 (1650), 270 nm (19160)

In yet another embodiment of the present invention, the novel compound m-fluorobenzyl n-butylxanthate is a pale yellow liuid having molecular formula $C_{12}H_{15}FOS_2$ and having the following properties:
Physical state: Pale yellow liquid
Molecular formula: $C_{12}H_{15}FOS_2$
$^1$H NMR: (CDCl$_3$, 200 MH$_z$) $\delta$1.0 (3H, m), 1.42 (2H, m), 1.75 (2H, m), 4.60 (2H, t, j=7.0 Hz), 4.35 (2H, s) and 6.95–7.20 (4H, m).
IR (Neat): $\nu_{max}$ 2960, 2931, 1615, 1590, 1460, 1240 and 1045 cm$^{-1}$
EIMS (70 eV): m/z 258
UV (MeOH): $\lambda_{max}$ 210($\epsilon$ 37105), 218 (356660) and 280 nm (27354)

In yet another embodiment of the invention, the novel compound m-fluorobenzyl isobutylxanthate is a pale yellow liquid and having molecular formula $C_{12}H_{15}FOS_2$ and having the following properties:
Physical state: Pale yellow liquid
Molecular formula: $C_{12}H_{15}FOS_2$
$^1$H NMR: (CDCl$_3$, 200 MH$_z$) $\delta$1.0 (6H, d, J=7.0 Hz), 2.12 (1H, m), 4.34 (4H, brs), and 6.92–7.22 (4H, m).
IR (Neat): $\nu_{max}$ 2964, 2937, 1620, 1585, 1472, 1230, 1165 and 1030 cm$^{-1}$
EIMS (70 eV): m/z 258
UV (MeOH): $\lambda_{max}$ 214($\epsilon$ 37190), 220 (35674) and 274 nm (27378)

One more embodiment of the invention provides a new use of analogues of alkylxanthates of formulae 1 to 6 of the drawings as insect growth regulators for the integrated pest management (IPM) and the analogues of alkylxanthates used are ethylene bis(isobutyl xanthate), methylene bis (n-butyl, xanthate), methylene bis (tetrafurfurylxanthate), p-xylene bis (n-butylxanthate) and m-Fluorobenzyl isobutylxanthate, the structural formulae of the above compounds are shown in the FIGS. 4, 5, 1, 6, 2 and 3 of the drawings respectively.

In still another embodiment of the invention, the alkyl xanthate controls the growth of the agricultural pests is *Spodoptera litura*, and *Helicover armigera*.

In still another embodiment the amount of alkylxanthates used as insect growth regulator is ranging from 50 $\mu$g to 100 $\mu$g per insect. (topical application on III instar larvae) and 5 to 25 $\mu$g oral feeding and the larval mortality rate is in the range between 50 to 90%.

In yet another embodiment the analogues of alkylxanthates are used as an antifeedant for the integrated pest management.

In yet another embodiment the amount of analogues of alkyl xanthates used for protecting the leafs are in the range between 15 to 50 micro grams per sq.cm of the leaf area.

In yet another embodiment the analogues of alkylxanthates used are ethylene bis(isobutyl xanthate), methylene bis (n-butyl xanthate), methylene bis (tetrafurfurylxanthate), p-xylene bis (n-butyl xanthate) and m-Fluorobenzyl n-butylxanthate and m-Fluorobenzyl isobutylxanthate.

In yet another embodiment of the invention, the alkyl xanthate acts against the ploy phagous pests, *Spodotera litura* (Tabaco caterpillar) and controls the consumption of the leaf by the pests.

In further embodiment the present invention provides a process for the preparation of analogues of alkyl xanthates useful as an antifeedant and as insect growth regulators, said process comprising:
(a) refluxing, KOH with an alcohol followed by adding carbondisulphide to get a yellow crystalline compound namely potassium-O-alkylxanthate,
(b) reacting the potassium-O-alkylxanthate in the presence of ketone with a bromide derivative selected from methylene di bromide, ethylene di bromide, p-Xylene dibromide or m-flurobenzyl bromide, filtering and removing the ketone under reduced pressure to obtain corresponding alkylxanthate compounds with the yield ranging from 70 to 80%.

In still another embodiment refluxing is carried out at a 0° C.

In one more embodiment of the invention provides a novel composition used as an insect growth regulator and an antifeedant for the integrated pest management, said composition comprising an effective amount of alkylxanthate and analogues of alkylxanthates with an additive.

In still another embodiment the analogues of alkyl xanthate is selected from ethylene bis(isobutyl xanthate), methylene bis (n-butyl xanthate), methylene bis (tetrahydrofurfuryl xanthate), p-xylene bis (n-butyl xanthate), m-Fluorobenzyl n-butylxanthate and m-Fluorobenzyl isobutylxanthate or mixture thereof.

In still another embodiment the additive is a solvent, i.e. $C_9$, cycloxonone, acetone, ethyl methyl ketone etc., with emulsifier piperonyl butoxide (5%).

In yet another embodiment, the ratio of the additive to the active ingredients is in the ratio ranging from 80 to 95%.

In yet another embodiment, the amount required for controlling the antifeedant activity is 30 to 60 $\mu$g/sq.cm.

In yet another embodiment, the amount required for use as insect growth regulators activity is 50 to 100 $\mu$g/insect (Topical) or 5 to 25 $\mu$g oral feeding.

The following examples are given merely to understand the invention clearly and these examples should not be construed to limit the scope of invention in any manner.

EXAMPLES

Preparation of bis (alkylxanthates): Into a 100-ml round-bottomed flask, fitted with a reflux condenser, placed 1.05 gm (0.0187 mol) of KOH pellets was added excess amount (0.072 mol) of alcohol and the reaction mixture was refluxed for 1 hr. The reaction mixture was cooled and decanted the liquid from the residual solid into another dry 100-ml R.B flask. To this cold reaction mixture 1.37 gm (0.0187 mol, 1.08 ml) of carbon disulfide was added slowly with constant stirring to yield yellow crystalline compound potassium-O-alkylxanthate (yield 80–90%).

To the above potassium-O-alkylxanthate (0.01 mol) in a 50 ml of acetone was added methylene di bromide 0.869 gm (0.348 ml, 0.005 mol) or ethylene di bromide 0.939 gm (0.52 ml, 0.005 mol) and refluxed for one hour. The reaction sets in within 15 minutes and the yellow reaction mixture becomes white owing to the separation of KBr. Then the reaction mixture was filtered, acetone was removed under vacuum. After usual workup n = 1 methylene bis (alkylxanthate)
n = 2 ethylene bis (alkylxanthate)

Here R=alkyl group, Aryl group n=1, 2 afforded bis (alkylxanthate) (yield 75 to 90%) showed in Table 1.

TABLE 1

| Compound No. | Compound Name | R | n |
|---|---|---|---|
| 1 | Ethylene Bis(iso-butylxanthate) | Isobutyl | 2 |
| 22 | Methylene Bis(n-butylxanthate) | n-butyl | 1 |
| 23 | Ethylene Bis(2°-butylxanthate) | 2°-butyl | 2 |
| 24 | Methylene Bis(2°-butylxanthate) | 2°-butyl | 2 |
| 5 | Ethylene Bis(benzyl-xanthate) | Benzyl | 2 |
| 3 | Ethylene Bis(n-butylxanthate) | n-butyl | 2 |
| 25 | Methylene Bis(tetra-hydrofurfuryl alcohol) | Tetrahydro furfuryl | 1 |

TABLE 1-continued

| Compound No. | Compound Name | R | n |
|---|---|---|---|

(structure shown)

Here R = alkyl group

Preparation of p-xylene bis (alkylxanthates): A mixture of potassium-O-alkylxanthate (0.01 mol) and p-xylene dibromide (0.005 mol) in a 50 ml of acetone refluxed for one hour. The reaction sets in within 15 minutes and the yellow reaction mixture becomes white owing to the separation of KBr. Then the reaction mixture was filtered, acetone was removed under vacuum. After usual workup yielded p-xylene bis (alkylxanthate) (yield 75–85%) showed in Table 2.

TABLE 2

| Compound No. | Compound Name | R |
|---|---|---|
| 12 | p-Xylene Bis (n-butylxanthate) | n-butyl |
| 26 | p-Xylene Bis (2°butylxanthate) | 2°-butyl |

Preparation of m-fluorobenzyl alkylxanthates: A mixture of potassium-O-alkylxanthate (0.01 mol) and m-fluorobenzyl bromide (0.01 mol) in a 50 ml of Here R=alkyl group acetone refluxed for one hour. The reaction sets in within 15 minutes and the yellow reaction mixture becomes white owing to the separation of KBr. Then the reaction mixture was filtered, acetone was removed under vacuum. After usual workup yielded m-fluorobenzyl alkylxanthate (yield 70–80%) showed in Table 3.03.

TABLE 3

| Compound No | Compound Name | R |
|---|---|---|
| 27 | m-Fluorobenzyl (n-butylxanthate) | n-butyl |
| 28 | m-Fluorobenzyl (Isobutylxanthate) | Isobutyl |

Preparation of organophosphorus compounds: A mixture of potassium-O-alkylxanthate (0.01 mol) and O,O-diethyl thio phosphonyl chloride (0.01 mol) in a 50 ml of acetone refluxed for one hour. The reaction sets in within 15 minutes and the yellow reaction mixture becomes white owing to the separation of KCl. Then the reaction mixture was filtered, acetone was removed under vacuum. After usual workup yielded O,O-diethyl thiophosphate alkylxanthate (yield 70–80%) showed in Table 3.04.

Here R=alkyl group, aryl group

TABLE 4

| Compound No. | Compound Name | R |
|---|---|---|
| 29 | O,O-diethyl thiophospate isobutylxanthate | Isobutyl |
| 30 | O,O-diethyl thiophospate 2°-butylxanthate | 2°-butyl |
| 10 | O,O-diethyl thiophospate n-butylxanthate | n-butyl |
| 31 | O,O-diethyl thiophospate phenethylxanthate | Phenethyl |

Biological activities

Methodology for LARVICIDAL activity:

To determine the efficacy of different analogues of Alkylxanthates against mosquito larvae, standard procedures as recommended by World Health Organization (1981) were followed with minor modifications. The desired concentration of the test solution was obtained by adding 1 ml of an appropriate stock solution to 249 ml of tap water in 500 ml beaker. Test solutions of different concentrations were prepared by diluting the stock solution in dechlorinated and filtered tap water followed by thorough mixing. Tween—80 [Poly (oxyethylene)$_n$—sorbitan monooleate] was used as an emulsifier at the concentration of 0.002% (v/v) to the final test solution whenever required. Control solutions were prepared in tapwater using acetone or ethanol and Tween—80 (0.002%). To each of the test concentrations, 25 late third or early fourth instar larvae which were acclimatized earlier were added. At least three replicates of each of the tests were made. Based on the results, five to ten suitable concentrations, which produced 10 to 100% mortality, were selected for detailed study and for calculating LC$_{50}$ values. Mortality was observed 24 hours after exposing the larvae to test solutions and the data was corrected for control mortality if any, by using Abbot's formula (Abbot 1925). All tests were carried out at a room temperature maintained at 28±1° C.

Methodology For Developmental Inhibition On Mosquitoes:

The developmental inhibition potential of different analogues of Alkylxanthates a evaluated based on the method of Mulla et al., 1974. Experiments were carried out with second, third, fourth instar larvae and pupae. Initially, to each of the 500 ml beakers containing wide range of test concentrations, 25 larvae were added. Based on the results, five to ten suitable concentrations, which produced 10 to 100% growth inhibition, were selected for detailed study. The data of at least three to four replicates each of three separate experiments was subjected to statistical analysis. Observations on abnormalities in larvae, pupae and adult emergence were made until 100% emergence in controls. All the experiments were performed at room temperature.

BRINE SHRIMP BIOASSAY:

Brine shrimp (Artemia salina) eggs were hatched in a shallow rectangular dish filled with artificial seawater, which was prepared with commercial salt mixture and double distilled water. A plastic divider were several 2-mm holes was clamped in the dish to make two unequal compartments. The eggs were sprinkled into the larger compartment that was darkened, while the smaller compartment was illuminated. After 48 hours the phototropic nauplii were collected by pipette from the lighted side, being separated by the divider from their shells.

Twenty shrimps were transferred to each sample vial and artificial seawater was added to make 5 ml. The nauplii can be counted macroscopically in the stem of the pipette against a lighted back ground. A drop of dry yeast suspension (3 µg in 5 ml artificial seawater) was added as food to each vial (Meyer, et al., 1982). Survivors were counted with the aid of a 3×magnifying glass, after 24 hours, and the percent mortality at each concentration and control was determined. The 24 hour counts were more useful. During control deaths, the data was corrected using Abbot's formula.

STATISTICAL ANALYSIS

The average mortality and growth inhibition data of experiments was subjected to IBM AT 386 computer analysis at our laboratory for calculating LC$_{50}$, LD$_{50}$, EC$_{50}$, ED$_{50}$, etc., and other statistical data. The software used was developed by Reddy et al., 1992.

Methodology for Antifeedant activity:

Tobacco caterpillar, Spodoptera litura F., larvae will be reared on Ricinus cummunis L. leaves at 27° C. and 65–70% R.H. Known area (cm$^2$) of leaf disks were painted with exact amount of pure compound (dissolved in acetone) and were dried at room temperature till the carrier solvent evaporated. For each concentration 5 to 6 replicates were prepared and experiments were conducted individually. Control disks were dipped in carrier solvent (acetone) alone. Third instar larvae weighing 200–250 mg are selected from stock culture, starved for 4 hr, and will be used individually for the assay of antifeedant activity. After 12 and 24 hours, leaf area meter was used to measure the consumed area of treated and untreated leaves. Based on the data the percent protection of individual compound was calculated. All these properties were compared with well-known antifeedant isolated from neem kernal 'Azadiractin'. Control and test larvae are transferred on fresh leaves and monitored till adult emergence to study the growth and behavioral aspects of the insect.

Methodology for Growth regulatory activity:

In continuation to Anteefedant experiments, the larvae (leaf consumed along with compound-calculated) were individually monitored till adult emergence. Based on the formation of normal, abnormal pupae, normal adult emergence and abnormal adult emergence were recorded and calculated the growth regulatory activity of the compound in comparison with standard. Relative inhibition 50 values of alkylxanthates on Spodoptera litura and Helicoverpa armigera were statistically analysed.

Results
1. Larvicidal activity of xanthates and its analogues against IV instar larvae of *Aedes aegypti*

| S. No. | Compound | $LC_{50} \pm$ S.E. (mg/l) |
|---|---|---|
| 1. | Ethylene bis (isobutylxanthate) | 8.06 ± 0.22 |
| 2. | Methylene bis (n-butylxanthate) | 5.33 ± 0.97 |
| 3. | Methylene bix (tetrahydrofurfurylxanthate) | 3.77 ± 0.59 |
| 4. | p-Xylene bis (n-butylxanthate) | 7.35 ± 0.51 |
| 5. | m-Fluorobenzyl n-butylxanthate | 12.53 ± 1.24 |
| 6. | m-Fluorobenzyl isobutylxanthate | 11.78 ± 2.35 |

II. Developmental Inhibition activity of xanthates and its analogues against third instar larvae of *Aedes aegypti* The sub lethal concentrations of all the analogues [$LC_{10}$ to $LC_{20}$ concentrations] have exhibited developmental inhibition on mosquito, *Aedes aegypti*. Abnormal pupal formation and pupal case attachment to emerged adults (leads to mortality) were quite common in most of the xanthates.

III. Toxic activity of xanthates and its analogues against Brine shrimp, *Artemia salina*

| S. No. | Compound | $LC_{50} \pm$ S.E. (mg/l) |
|---|---|---|
| 1. | Ethylene bis (isobutylxanthate) | 25.78 ± 2.90 |
| 2. | Methylene bix (n-butylxanthate) | 34.65 ± 3.91 |
| 3. | Methylenebix (tetrahydrofurfurylxanthate) | 5.63 ± 0.62 |
| 4. | p-Xylene bis (n-butylxanthate) | 45.23 ± 5.63 |
| 5. | m-fluorobenzyl n-butylxanthate | 19.00 ± 2.83 |
| 6. | m-fluorobenzyl isobutylxanthate | 22.54 ± 3.26 |
| 7. | Standard 'Chamtothecin' | 2.53 ± 0.43 |

IV. Antifeedant activity of xanthate and its analogues against late third instar of *Spodoptera litura*

Data represented as the mean of five replicates in three different sets of experiments.

A,I = Anti-feedent Index = $\frac{(Control\ consumption) - (Treated\ consumption)}{(Control\ consumption) + (Treated\ consumption)} \times 100$ Normal and control worms consumed 45–50% leaf in 12 hours and 87–95% leaf consumption in 24 hours.

Figure 9:
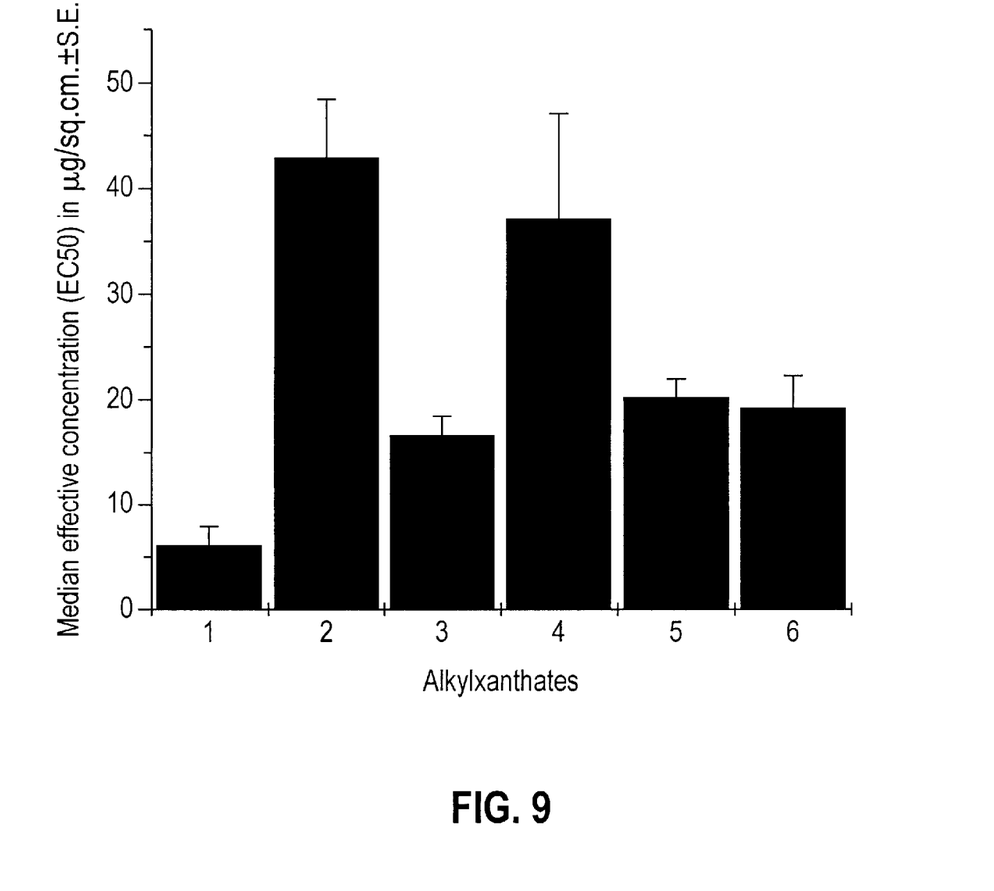
FIG. 9 shows a comparison of the concentration of xanthates and its analogues required for 50% leaf protection.
Figure 10:
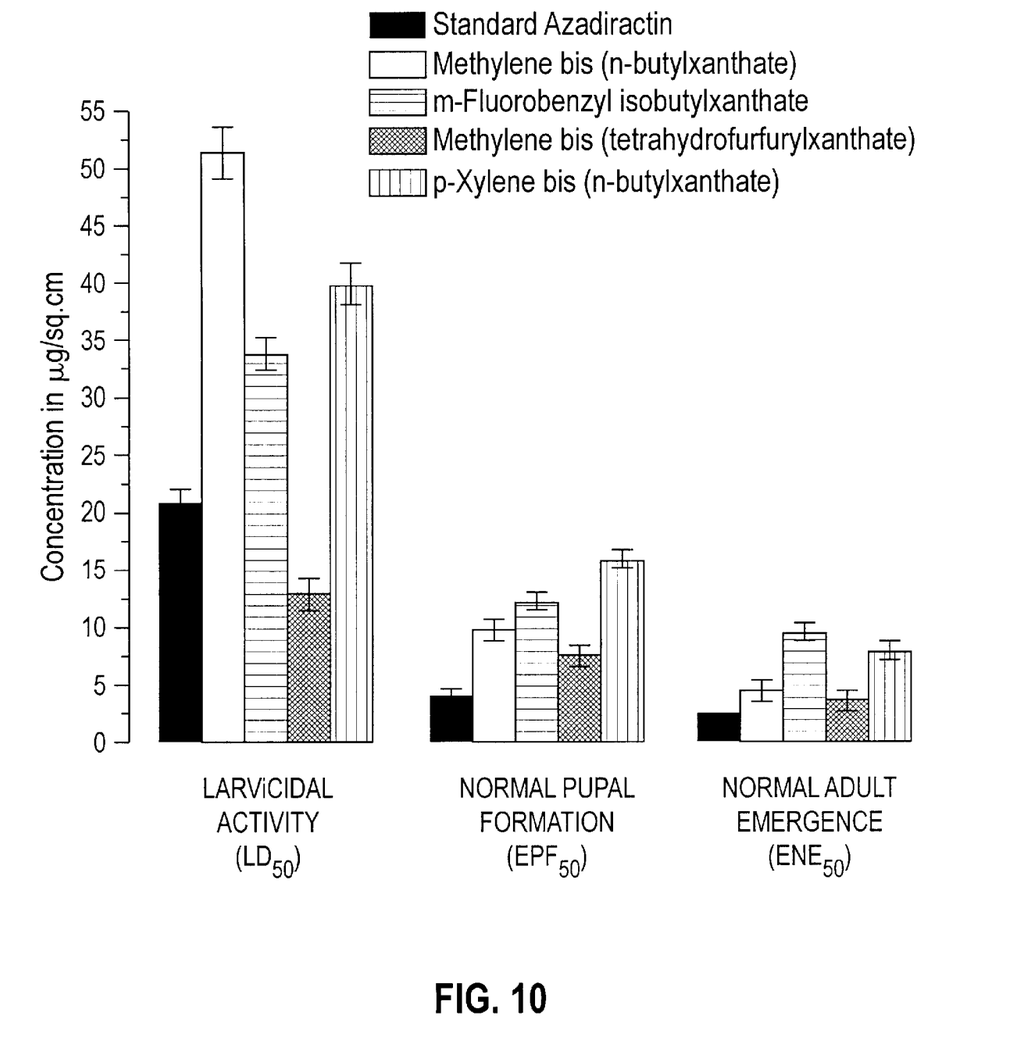
FIG. 10 shows a comparison concentration required for larvicidal activity and the onset of abnormal pupal formation and abnormal adult emergence of xanthates and its analogues.

It is concluded that the above alkylxanthates have exhibited similar kind of mode of action as Azadiractin. Though alkylxanthates have less active than Azadiractin but they can be very easily synthasized and possessing quick biodegradability. The above results were obtained through oral feeding. Similar activities were also observed when these larvae were treated topically with known amount of compounds. These experiments are also conformed that the mode of action is similar to Azadiractin. The results of these tests are summarized in FIGS. 9 and 10. In FIG. 9, the concentration of xanthates and its analogues required for 50% leaf protection is shown. The tested compounds include the standard compound, ethylene bis(isobutylxanthate), methylene bis(n-butylxanthate), methylene bis (tetrahydrofurfurylxanthate), p-xylene bis(n-butylxanthate) and m-fluorobenzyl isobutylxanthate. FIG. 10 shows lethal dose the $LD_{50}$ $EPF_{50}$ and $ENE_{50}$ of different alkylxanthates tested.

Bio-evaluation on *Helicoverpa armigera* (an Agricultural pest) Topical application of analogues)

Our earlier studies exhibited the analogues of alkylxanthates as an antifeedents and insect growth regulator properties against agricultural pest *Spodoptera litura*.

Further experiments were performed on *Helicoverpa armigera* (Hubner), a lepidopteron pest was used as an experimental modal to reconfirm the IGR activities of alky-

| Compound code | Conc. in μg/sq. cm. | Percent leaf consumption | | | Concentration required for 50% leaf protection $EC_{50}$ in μg/cm² ± S.E. |
|---|---|---|---|---|---|
| | | 12 hr | 24 hr | A.I. | |
| Standard Azadiractin | 20 | 4.2 | 12.7 | 76.42 | 6.34 ± 1.77 |
| | 15 | 16.4 | 27.6 | 54.98 | |
| | 10 | 18.6 | 33.3 | 48.09 | |
| | 5.0 | 33.7 | 57.2 | 24.84 | |
| Ethylene Bis (isobutylxanthate) | 65 | 9.3 | 25.2 | 58.07 | 42.46 ± 5.76 |
| | 50 | 22.4 | 45.9 | 34.85 | |
| | 35 | 36.1 | 62.7 | 20.48 | |
| | 20 | 60.2 | 80.7 | 8.14 | |
| Methylene Bis (n-butylxanthate) | 30 | 0 | 7.5 | 85.37 | 17.11 ± 1.36 |
| | 25 | 3.5 | 20.7 | 64.22 | |
| | 20 | 22.5 | 45.6 | 35.14 | |
| | 15 | 35.2 | 60.4 | 22.27 | |
| | 10 | 48.55 | 85.1 | 5.50 | |
| Methylene Bis (tetrahydrofurfuryl alcohol) | 50 | 22.1 | 45.5 | 35.23 | 37.21 ± 9.67 |
| | 35 | 25.9 | 47.3 | 33.52 | |
| | 25 | 31.5 | 60.2 | 22.42 | |
| | 12.5 | 48.6 | 80.6 | 8.20 | |
| p-Xylene Bis (n-butylxanthate) | 25 | 20.5 | 24.6 | 58.86 | 29.45 ± 1.76 |
| | 20 | 35.2 | 57.6 | 24.51 | |
| | 15 | 62.4 | 84.3 | 5.97 | |
| | 10 | 57.3 | 90.2 | 2.59 | |
| m-Fluorobenzyl isobutylxanthate | 25 | 12.5 | 32.8 | 48.67 | 19.65 ± 2.99 |
| | 20 | 24.7 | 53.6 | 27.86 | |
| | 15 | 33.24 | 68.7 | 16.07 | |
| | 10 | 50.4 | 75.2 | 11.63 | | lxanthates. Once again the present results proved that the importance of these compounds as potential candidates as Insect Growth Regulators (IGR) against lipidopteron pests. The activity of Azadiractin (standard compound) and alkylxanthates has a similar mode of action i.e., less larvicidal activity, minimized in the formation of normal pupae and emergence of normal adults.

The genera Helicoverpa (Heliothis) is one of the most important Lepidopteron pest of both subsistence and cash crops in the new and old worlds. *Helicoverpa armigera* (Hubner), commonly referred to as the American bollworm or gram pod borer, is the most widely distributed of the group occurring in Africa, Asia, Australia, Oceania and Europe. The polyphagous larvae attack cotton, maize, sorghum, sunflower, tomato, okra and a range of legumes.

In India, annual loses to pigeonpea and chickpea alone may exceed US$ 300 million (Reed and power, 1982), and a more recent estimate by Mehrotra (Indian Agricultural Research Institute, unpublished) suggests that total loses to pluses and cotton are likely to be more than US$ 530 million per annum.

| Sample Code | Conc. ($\mu g$/Insect) | No. Insects used for assay | Larval mortality (%) | Pupal Formation | | | Adult emergence | | | Non emergence |
|---|---|---|---|---|---|---|---|---|---|---|
| | | | | Normal pupa | Abnormal Pupa | Pupal Mortality | Normal adults | Abnormal adults | Intermediates | |
| Methylene Bis (n-butylxanthate) | 100 | 20 × 5 | 61 | 0 | 22 | 17 | 0 | 0 | 2 | 20 |
| | 75 | 20 × 5 | 49 | 0 | 27 | 24 | 0 | 1 | 2 | 24 |
| | 50 | 20 × 5 | 28 | 12 | 32 | 28 | 8 | 9 | 6 | 21 |
| | 35 | 20 × 5 | 12 | 27 | 28 | 33 | 17 | 11 | 18 | 9 |
| | 20 | 20 × 5 | 7 | 52 | 36 | 5 | 27 | 41 | 17 | 3 |
| O,O-diethyl thiophospate phenethyl xanthate | 100 | 25 × 4 | 92 | 0 | 6 | 3 | 0 | 1 | 0 | 5 |
| | 75 | 25 × 4 | 85 | 3 | 5 | 7 | 4 | 1 | 0 | 3 |
| | 50 | 25 × 4 | 71 | 5 | 11 | 9 | 5 | 7 | 2 | 2 |
| | 35 | 25 × 4 | 62 | 12 | 15 | 11 | 9 | 16 | 4 | 8 |
| | 25 | 25 × 4 | 47 | 23 | 13 | 17 | 15 | 7 | 5 | 9 |
| p-Xylene Bis (n-butylxanthate) | 100 | 20 × 5 | 85 | 0 | 6 | 15 | 0 | 1 | 1 | 4 |
| | 75 | 20 × 5 | 71 | 5 | 7 | 17 | 0 | 2 | 2 | 8 |
| | 50 | 20 × 5 | 56 | 10 | 13 | 21 | 5 | 13 | 5 | 4 |
| | 35 | 20 × 5 | 42 | 12 | 18 | 28 | 9 | 12 | 3 | 6 |
| | 20 | 20 × 5 | 18 | 39 | 27 | 16 | 33 | 19 | 7 | 5 |
| Control | 100 | 25 × 4 | 3 | 97 | 0 | 0 | 94 | 0 | 0 | 3 |
| Azadiractin | 50 | 25 × 4 | 91 | 0 | 5 | 4 | 0 | 2 | 2 | 1 |
| | 35 | 25 × 4 | 68 | 8 | 12 | 12 | 2 | 6 | 4 | 3 |
| | 20 | 25 × 4 | 47 | 13 | 27 | 13 | 10 | 17 | 5 | 8 |
| | 10 | 25 × 4 | 26 | 33 | 23 | 18 | 18 | 21 | 10 | 7 |
| | 5 | 25 × 4 | 11 | 47 | 31 | 11 | 38 | 18 | 20 | 2 |
| | 2.5 | 25 × 4 | 2 | 62 | 28 | 8 | 51 | 26 | 13 | 0 |

The analogues of alkylxanthates has been proved as insect growth regulators (IGR) against two different lepidopteron pests as similar to Azadiractin (standard compound) a natural product isolated from neem seed kernel. They have simple structures unlike Azadiractin and possessing same kind of mode of action which can be synthesized easily in the laboratory.

VI. Bio-evaluations on Agricultural pest, *Spodoptera litura* (Topical application of xanthate analogues)

| Sample Code | Conc. ($\mu g$/Insect) | No. Insects used for assay | Larval mortality (%) | Pupal Formation | | | Adult emergence | | | Non-emergence |
|---|---|---|---|---|---|---|---|---|---|---|
| | | | | Normal pupa | Abnormal pupa | Pupal Mortality | Normal adults | Abnormal adults | Intermediates | |
| Methylene bis (n-butylxanthate) | 100 | 20 × 5 | 86 | 0 | 14 | 14 | 0 | 0 | 0 | 14 |
| | 75 | 20 × 5 | 72 | 0 | 28 | 25 | 0 | 1 | 2 | 25 |
| | 50 | 20 × 5 | 57 | 5 | 38 | 24 | 5 | 6 | 8 | 9 |
| | 35 | 20 × 5 | 21 | 25 | 54 | 26 | 7 | 23 | 23 | 25 |
| | 20 | 20 × 5 | 0 | 47 | 53 | 17 | 24 | 27 | 32 | 2 |
| | 10 | 20 × 5 | 0 | 52 | 48 | 8 | 36 | 22 | 34 | 1 |
| | 5 | 20 × 5 | 0 | 59 | 41 | 5 | 41 | 26 | 28 | 0 |
| M-Fluoro benzyl isobutyl | 100 | 20 × 5 | 96 | 0 | 4 | 4 | 0 | 0 | 0 | 0 |
| | 75 | 20 × 5 | 83 | 9 | 8 | 13 | 0 | 3 | 1 | 2 |
| | 50 | 20 × 5 | 70 | 13 | 15 | 9 | 3 | 11 | 5 | 4 |

-continued

| Sample Code | Conc. (μg/Insect) | No. Insects used for assay | Larval mortality (%) | Pupal Formation Normal pupa | Abnormal pupa | Pupal Mortality | Adult emergence Normal adults | Abnormal adults | Intermediates | Non-emergence |
|---|---|---|---|---|---|---|---|---|---|---|
| xanthate | 35 | 20 × 5 | 56 | 25 | 19 | 7 | 17 | 14 | 6 | 0 |
| | 20 | 20 × 5 | 27 | 43 | 30 | 4 | 39 | 22 | 8 | 0 |
| | 10 | 20 × 5 | 10 | 58 | 32 | 8 | 49 | 29 | 4 | 1 |
| | 5 | 20 × 5 | 3 | 73 | 24 | 3 | 50 | 32 | 2 | 0 |
| Methylene bis (tetrahydro-furfuryl-xanthate) | 100 | 25 × 4 | 98 | 0 | 2 | 1 | 0 | 1 | 0 | 0 |
| | 75 | 25 × 4 | 91 | 2 | 7 | 5 | 2 | 2 | 0 | 2 |
| | 50 | 25 × 4 | 80 | 7 | 13 | 4 | 4 | 9 | 3 | 1 |
| | 35 | 25 × 4 | 71 | 19 | 10 | 7 | 9 | 11 | 2 | 3 |
| | 20 | 25 × 4 | 59 | 25 | 16 | 7 | 15 | 17 | 21 | 2 |
| | 10 | 25 × 4 | 46 | 44 | 10 | 6 | 28 | 19 | 1 | 2 |
| | 5 | 25 × 4 | 36 | 58 | 6 | 5 | 37 | 22 | 0 | 3 |
| p-Xylene bis (n-butylxanthate) | 100 | 20 × 5 | 95 | 0 | 5 | 4 | 0 | 0 | 1 | 2 |
| | 75 | 20 × 5 | 86 | 3 | 11 | 10 | 0 | 2 | 2 | 2 |
| | 50 | 20 × 5 | 71 | 8 | 21 | 14 | 2 | 13 | 3 | 1 |
| | 35 | 20 × 5 | 59 | 12 | 29 | 13 | 9 | 17 | 2 | 4 |
| | 20 | 20 × 5 | 20 | 59 | 21 | 5 | 25 | 36 | 14 | 5 |
| | 10 | 20 × 5 | 5 | 72 | 23 | 3 | 44 | 38 | 10 | 1 |
| | 5 | 20 × 5 | 0 | 85 | 15 | 2 | 59 | 29 | 10 | 0 |
| Control | 100 | 25 × 4 | 5 | 95 | 0 | 0 | 94 | 0 | 0 | 1 |
| Standard Azadiractin | 75 | 25 × 4 | 96 | 0 | 4 | 4 | 0 | 0 | 0 | 0 |
| | 50 | 25 × 4 | 88 | 7 | 5 | 8 | 0 | 2 | 2 | 1 |
| | 35 | 25 × 4 | 72 | 10 | 18 | 16 | 2 | 6 | 4 | 2 |
| | 20 | 25 × 4 | 52 | 19 | 29 | 10 | 10 | 17 | 11 | 3 |
| | 10 | 25 × 4 | 30 | 38 | 32 | 7 | 28 | 21 | 14 | 1 |
| | 5 | 25 × 4 | 9 | 45 | 34 | 11 | 38 | 19 | 20 | 2 |
| | 2.5 | 25 × 4 | 0 | 62 | 38 | 6 | 47 | 26 | 21 | 6 |

We claim:
1. Compounds of alkylxanthates namely
   (i) methylene Bis (tetrahydrofurfuryl xanthate)
   (ii) m-Fluorobenzyl n-butylxanthate and
   (iii) m-Fluorobenzyl isobutylxanthate having the structural formulae (i), (ii) and (iii) as shown below:

for use in agricultural applications.

2. Compounds as claimed in claim 1, wherein said compounds have the following properties on lepidopteron pest as
   (a) larvicidal,
   (b) antifeedant, and
   (c) insect growth regulator.

3. Compounds as claimed in claim 1, wherein said compounds possess toxicity towards brine shrimp and mosquitoes.

4. Compounds as claimed claim 1, wherein said compounds control the growth of at least one of the agricultural pests *Spodoptera litura,* and *Helicover armigera.*

5. Compounds as claimed in claim 1, wherein an effective amount of alkylxanthates used as an insect growth regulator ranges from 50 μg to 100 μg/insect for topical application on III instar larvae and 5 to 25 μg/insect for oral feeding.

6. Compounds as claimed claim 1, wherein a larval mortality rate is in a range between 50 to 90%.

7. Compounds as claimed in claim 1, wherein an effective amount of alkylxanthate analogues for protecting leaves is in a range between 15 to 50 μg/cm² of leaf area.

8. The methylene Bis (tetrahydrofurfuryl xanthate) compound as claimed in claim 1, wherein said compound is a colorless liquid having a molecular formula $C_{13}H_{20}O_4S_4$.

9. The m-fluorobenzyl n-butylxanthate compound as claimed in claim 1, wherein said compound is a pale yellow liuid having a molecular formula $C_{12}H_{15}FOS_2$.

10. The m-fluorobenzyl isobutylxanthate compound as claimed in claim 1, wherein said compound is a pale yellow liquid and having a molecular formula $C_{12}H_{15}FOS_2$.

11. A method for regulating insect growth comprising:
    applying an alkylxanthate analog selected from the compounds having the structural formulas as set forth below:

-continued ii iii v vi

12. The method as claimed in claim 11, wherein the alkylxanthate analog controls the growth of at least one of the agricultural pests *Spodoptera litura* and *Helicover armigera*.

13. The method as claimed in claim 11, wherein an effective amount of the alkylxanthate analogue used as an insect growth regulator ranges from 50 μg to 100 μg/insect for topical application on III instar larvae and 5 to 25 μg/insect for oral feeding.

14. The method as claimed in claim 11, wherein a larval mortality rates ranges between 50 to 90%.

15. A method for inhibiting insect feeding comprising:
applying an alkylxanthate analog to leaves.

16. The method as claimed in claim 15, wherein the alkylxanthate analogues are applied to the leaves in amounts in the range between 15 to 50 μg/cm² of leaf area.

17. The method as claimed in claim 15, wherein alkylxanthate analog used is selected from the group consisting of ethylene bis(isobutyl xanthate), methylene bis (n-butyl xanthate), methylene bis (tetrafurfurylxanthate), p-xylene bis (n-butyl xanthate), m-Fluorobenzyl n-butylxanthate and m-Fluorobenzyl isobutylxanthate.

18. The method as claimed in claim 15, wherein the alkylxanthate acts against ploy phagous pests, *Spodotera litura* (Tobaco caterpillar) and controls consumption of the leaves by insects.

19. A process for the preparation of analogues of alkyl xanthates useful as an antifeedant and as insect growth regulators, said process comprising:

a. refluxing, KOH with an alcohol followed by adding carbondisulphide to get a yellow crystalline compound namely potassium-O-alkylxanthate, b. reacting the potassium-O-alkylxanthate in the presence of ketone with a bromide derivative selected from methylene di bromide, ethylene di bromide, p-Xylene dibromide or m-flurobenxyl bromide, filtering and removing the ketone under reduced pressure to obtain corresponding alkylxanthate compounds with the yield ranging from 70 to 80%.

20. A process as claimed in claim 19 wherein, the refluxing is carried out at a 0° C.

21. A composition used as an insect growth regulator and an antifeedant for the integrated pest management, said composition comprising an effective amount of alkylxanthate or analogues of alkylxanthates with an additive.

22. A composition as claimed in claim 21, wherein the analogues of alkyl xanthate is selected from methylene bis (n-butyl xanthate), methylene bis (tetrahydrofurfuryl xanthate), p-xylene bis (n-butyl xanthate), m-Flurorbenzyl n-butylxanthate, m-Fluorobenzyl isobutylxanthate, and mixture thereof.

23. A composition as claimed in claim 21, wherein the additive is a solvent selected from the group consisting of $C_9$, cycloxonone, acetone, ethyl methyl ketone with emulsifier piperonyl butoxide (5%).

24. A composition as claimed in claim 23, wherein a ratio of the additive to the active ingredients is in a range between 80 to 95%.

25. A composition as claimed in claim 23, wherein the effective amount required for controlling the antifeedant activity is 30 to 60 μg/sq.cm.

26. A composition as claimed in claim 23, wherein the effective amount required for use as insect growth regulators activity is 50 to 100 μg/insect for topical or 5 to 25 μg/insect for oral feeding.

27. A composition as claimed in claim 23 wherein, the effective amount required for controlling the antifeedant activity is 30 to 60 μg/cm².

28. A composition as claimed in claim 23 wherein, the amount required for use is insect growth regulators activity is 50 to 100 μg/insect for topical application or 5 to 25 μg/insect for oral feeding.

* * * * *